United States Patent [19]

Okumoto et al.

[11] 4,087,249
[45] May 2, 1978

[54] PYROLYSIS APPARATUS FOR ANALYSIS

[75] Inventors: Tadaoki Okumoto, Inazawa; Tsugio Takeuchi; Shin Tsuge, both of Nagoya, all of Japan

[73] Assignee: Toyoda Gosei Co., Ltd., Japan

[21] Appl. No.: 752,324

[22] Filed: Dec. 20, 1976

[30] Foreign Application Priority Data

Dec. 26, 1975 Japan ............................ 51-157285
May 31, 1976 Japan ............................ 51-63320
Dec. 26, 1975 Japan ............................ 51-157286

[51] Int. Cl.² .................... G01N 31/12; G01N 31/08; G01N 25/24
[52] U.S. Cl. .......................... 23/253 PC; 23/254 R
[58] Field of Search ........ 23/230 PC, 253 PC, 254 R; 73/25, 23.1

[56] References Cited

U.S. PATENT DOCUMENTS

| | | |
|---|---|---|
| 3,703,355 | 11/1972 | Takahashi et al. ............ 23/230 PC |
| 3,753,654 | 8/1973 | Eggertsen ...................... 23/230 PC |
| 3,847,554 | 11/1974 | Su .................................. 23/230 PC |
| 3,898,041 | 8/1975 | Stephens ........................ 23/230 PC |

Primary Examiner—R.E. Serwin
Attorney, Agent, or Firm—Robert E. Burns; Emmanuel J. Lobato; Bruce L. Adams

[57] ABSTRACT

A pyrolysis apparatus comprising a pyrolysis heater and a pyrolysis tube, wherein the pyrolysis heater is of the vertical type. A sample basket being is disposed in the central portion in the lengthwise direction of the pyrolysis heater. A sample pyrolysis position is disposed inside the tube. A sample basket holder is provided at the upper end portion of the pyrolysis tube. The holder is provided with a detachable device for holding a sample basket connecting rod which facilitates free dropping of the sample basket to the sample pyrolysis position and a slit means are provided right under the central heating portion inside the pyrolysis tube so that the sample basket does not drop any more therefrom.

9 Claims, 13 Drawing Figures

PYROLYSIS APPARATUS FOR ANALYSIS

BACKGROUND OF THE INVENTION

The present invention relates to a pyrolysis apparatus for analysis (referred to as pyrolysis apparatus hereinafter) attached to one of analyzers, a gas chromatograph or CHN analyzer.

Figure 1:
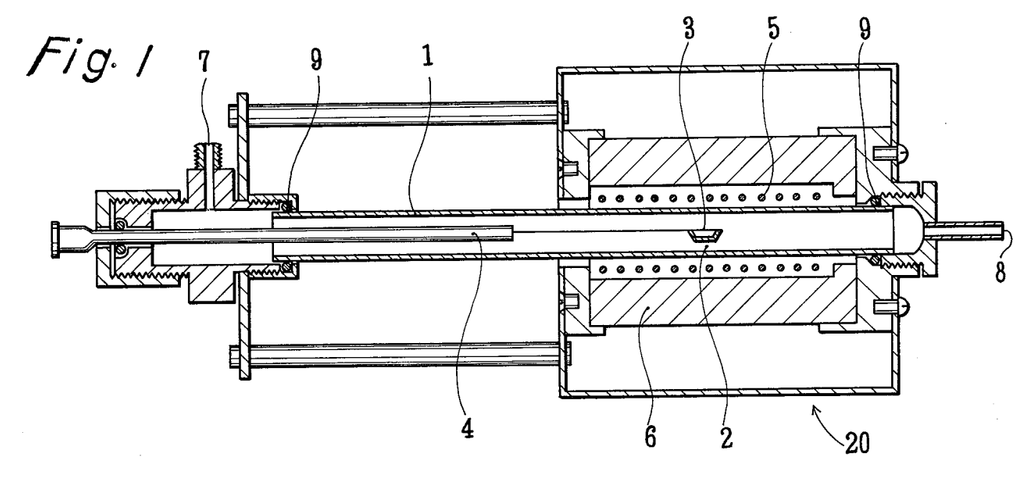
FIG. 1 is a vertical section view of a conventional pyrolysis apparatus.

As shown in FIG. 1, the degradation of high molecular material and analysis of a pyrolysis product directly introduced into a gas chromatograph has been conducted by manually moving a connecting rod 4 connected to a sample dish 3 made of platinum loaded with a sample for introducing it into a central heating portion, i.e., a sample pyrolysis position 2 inside a pyrolysis tube 1. The tube 1 is made of quartz glass and kept at a definite high temperature for pyrolyzing the sample thereat. For heating a pyrolysis heater 20, made with nichrome wire, is employed and its surroundings are insulated with fire brick 6. Inert gas is admitted into the tube 1 from an inlet 7 to an outlet 8. The inert gas flows therebetween and an O ring 9 provides a seal to prevent the gas from leaking out of the pyrolysis tube 1 and away from sample dish connecting rod 4.

This apparatus is disposed horizontally in use and the sample dish connecting rod 4 is introduced into the pyrolysis tube 1 in a horizontal position.

With such an apparatus as the above-mentioned, there have been errors made in analytical data between laboratories, workers or experiments due to the reason described below, so that it has been difficult to obtain good and accurate data available for repetition and reproduction thereof.

1. Due to manual pushing of the sample dish connecting rod the speed of, introducing of the sample into the pyrolysis tube can not be constant.
2. The sample is liable to spill from the sample dish on the way to the sample pyrolysis position.
3. When placing the sample dish at the sample pyrolysis position, the sample contacts the tube wall and heating of the sample becomes uneven because the sample dish connecting rod is long.

SUMMARY OF THE INVENTION

In view of the preceding, an object of the present invention is to provide a pyrolysis apparatus available of good analytical data for reproducibility.

Another object of the present invention is to provide a pyrolysis apparatus available of accurate quantitative analytical data.

A further object of the present invention will be clear with the undermentioned description and drawings.

DETAILED DESCRIPTION OF THE PREFERRED EMBODIMENTS OF THE INVENTION

According to drawings, examples of the present invention will be described below:

EXAMPLE 1

Figure 2:
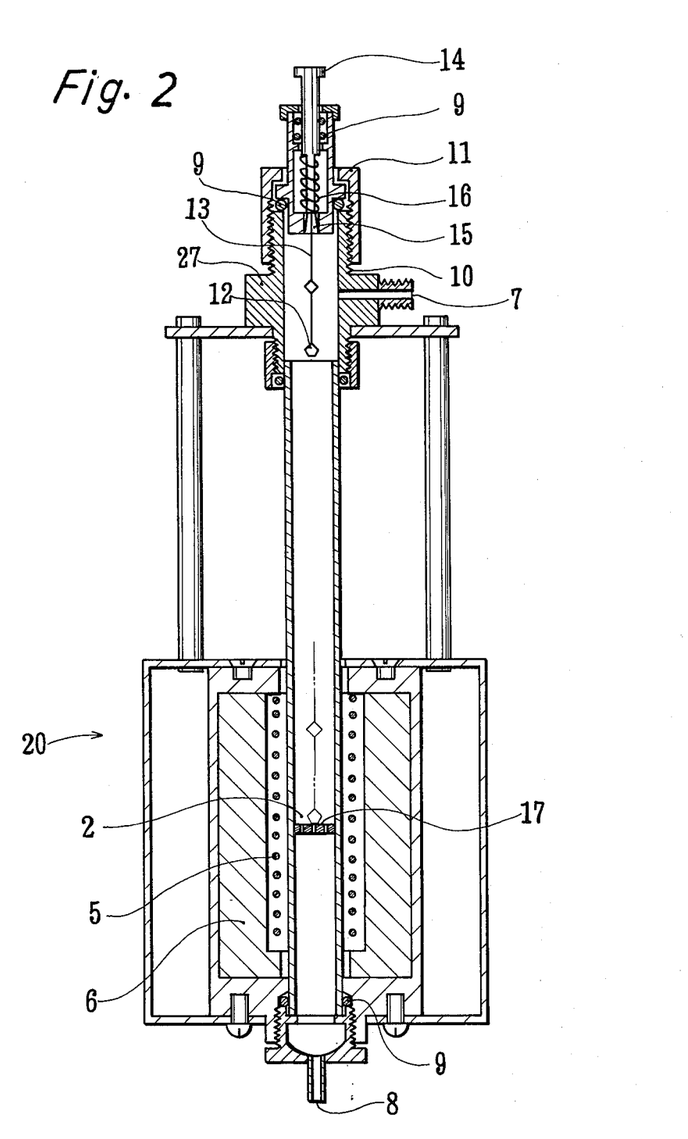
FIG. 2 is a vertical section view of a pyrolysis apparatus, as an example of the present invention.

In FIG. 2, a cap 11 is removed from a threaded portion 10 of a sample inserting pipe 27. With respect to the holding power for a sample basket 12 or open receptacle and a wire form sample basket connecting rod 13, the mouth of a detachable device 15 is opened by pressing a push button 14 taking advantage of the elastic stability of the detachable device 15, thus releasing the holding power therefor as later explained. At this time, inserting sample basket connecting rod 13 is inserted thereinto and releasing pressure on the push button 14, sample basket connecting rod 13 is releasably held by the detachable clamp-like device 15. Then, cap 11 attached with detachable device 15 is fitted an set on the threaded portion 10. Between the push button 14 and device 15 an O ring 9 seals to keep an air tight seal so as to prevent gas from leaking therebetween. The sample basket is made of platinum and is good for repeated use.

On the other hand, a pyrolysis heater 20 is of the vertical type and a nichrome heating wire thereof is surrounded with fire brick 6, in which a pyrolysis tube 1 made of quartz glass is placed. Inside the pyrolysis tube 1, inert gas flows from a inlet 7 to an outlet 8. At the central heating portion of the pyrolysis tube, i.e., right under a sample pyrolysis position 2, a slit plate 17 is arranged so that inert gas or gas pyrolyzed from the sample is able to go through.

When making an actual experiment, pressing of the push button 14 downwards and releases the holding power thereof by taking advantage of elastic the stability of detachable device 15. The mouth of the device is (see FIGS. 4 and 5) opened and the sample basket 12 loaded with a sample of about 0.1mg and the sample basket connecting rod 13 drop freely due to the force of gravity and the basket reaches the slit plate 17, on which the sample is pyrolyzed.

On reaching the slit plate, because of a small quantity (about 0.1mg) of the sample, though it does not seem to scatter, even when somewhat scattered it does not have an influence on the data.

Next a more detailed description will be made on the detachable device.

Figure 3:
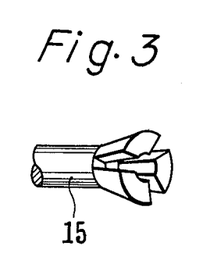
FIG. 3 is a fragmentary perspective view of a detachable device.
Figure 4:
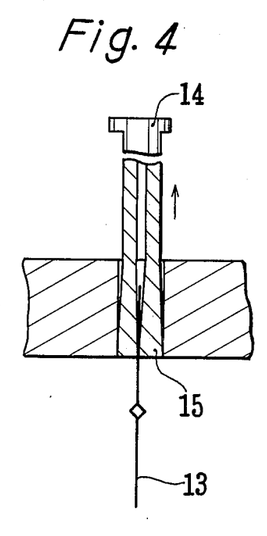
FIG. 4 is a cross section view of the detachable device in the state of holding the sample basket connecting rod.
Figure 5:
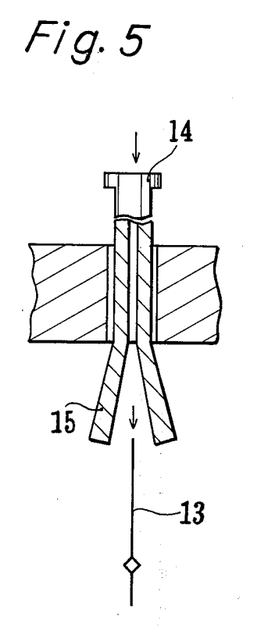
FIG. 5 is a cross section view of the detachable device in the state immediately after detaching the sample basket connecting rod.

FIG. 3 shows a perspective view of the open state of the clamp of the detachable device due to the elastic stability of the device when the push button 14 is pressed downwards. And, the clamping portion is divided into three parts, though it is by no means limited to three parts. FIG. 4 shows the state of the device upon releasing downward pressure on push button 14, with the sample basket connecting rod 13 pushed into the detachable device 15. When downward pressure on the push button is released the clamp-like device is restored to a raised position by the spring 16 and the clamp is closed. FIG. 5 shows the initial dropping state of the sample connecting rod 13 leaving from detachable device 15 upon pressing push of button 14 downwardly in conducting an experiment.

Next, function of the Example 1 will be described according to FIG. 2.

In FIG. 2, by pressing push the button 14 downwards, the mouth of the clamping portion of the detachable device 15 is opened and the sample basket or receptacle 12 loaded with a sample and the wire sample connecting rod drop and reach the slit plate 17 inside the pyrolysis tube 1, at which the position sample is pyrolyzed.

Figure 6:
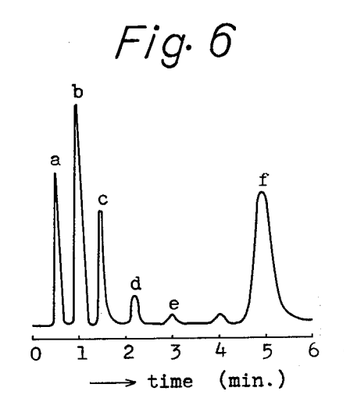
FIG. 6 illustrates a gas chromatogram pyrogram of polybutadiene determined with the pyrolysis apparatus of FIG. 2.
Figure 7:
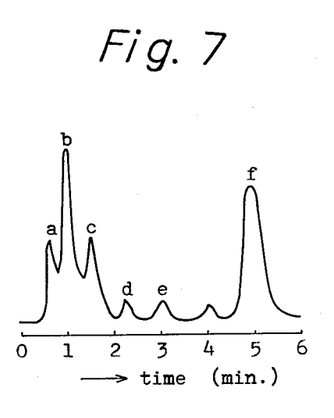
FIG. 7 illustrates a gas chromatogram of polybutadiene determined with the pyrolysis apparatus of FIG. 1.

FIG. 6 is a chromatogram determined by connecting to Model GCG-550F gas chromatograph manufactured by YANAGIMOTO SEISAKUSHO equipped with hydrogen flame ionizing detector, with a pyrolysis apparatus of Example 1 employed. FIG. 7 is a chromatograph determined by connecting to the identical Model GCG-500F gas chromatograph manufactured by YANAGIMOTO SEISAKUSHO, with the conventional pyrolysis apparatus employed. As a sample, 1, 2-polybutadiene on the market is employed and the pyrolysis temperature is 500 C. About 0.1mg of the sample is used. The determinating condition for gas chromatograph is applied as follows:

Bulking agent: Durapak (80 to 100 mesh)
Column: length: 2m
   inside-diameter: 3mm dia.
   material: cupper
   temperature: 30 C constant
Carrier gas: nitrogen Peak numbers of chromatograms on FIGS. 6 and 7 indicate pyrolysis products of *a*: methance, *b*: ethane, *c*: ethylene, *d*: propane, *e*: propylene and *F*: 1, 2-polybutadiene, respectively.

Compared with the conventional apparatus, the peaks of cracked products of methane, ethane and ethylene in Example 1's apparatus are clearly separated demonstrating instantaneous pyrolyzing of the sample. It can be said that the apparatus of the present invention obtains good results for analyzing the micro structure of high molecular compounds from these products.

Figure 8:
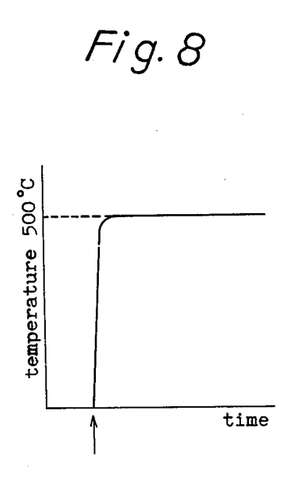
FIG. 8 is a curve for time-temperature in the sample in the pyrolysis apparatus of FIG. 2.
Figure 9:
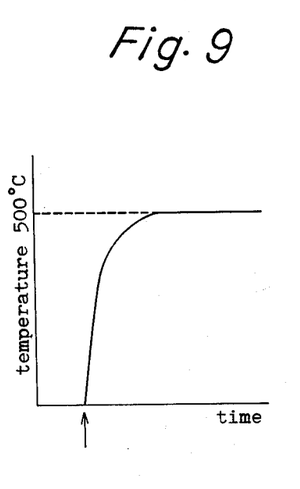
FIG. 9 is a curve for time-temperature in the sample in the pyrolysis apparatus of FIG. 1.

A reason for the good result in Example 1's apparatus as compared with the conventional apparatus, consideration can be made as follows:

FIGS. 8 and 9 show the effect of the heat capacity of the sample basket in Example 1 and the conventional sample plate on time variations in temperatures inside respective sample plate and sample basket. In FIG. 8, it is expected that heat capacity of the sample basket is small upon free dropping and that the sample is pyrolyzed with variations in time-temperature as shown in FIG. 8 because the time required for reaching the heating portion is short due to free dropping compared with that of the conventional manual introduction. For this reason, the apparatus is able to evenly pyrolyze the sample and considerably control secondary pyrolysis, so that clearly separated peaks seem to be developed as shown in FIG. 6. On the other hand, with the conventional apparatus, it is expected that when inserting the sample holder a certain heat capacity for preheating the metal portion as well as a certain time for inserting the holder are required, so that the sample is pyrolyzed with variations in time-temperature as shown in FIG. 9. For the reason, it takes time to increase the set temperature by 500° centigrade, and pyrolysis becomes uneven and liable to bring about secondary pyrolysis, so that as shown in FIG. 7 peaks of pyrolysis products are not clearly developed but an overlapped phenomenon seems to be developed at the bottom portion.

EXAMPLE 2

Figure 10:
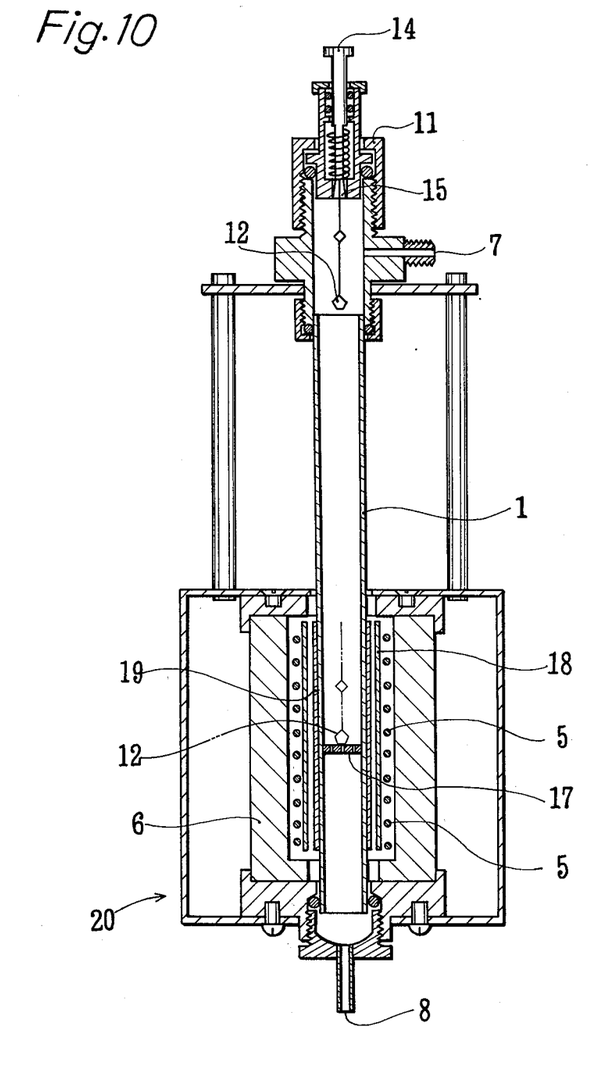
FIG. 10 is a vertical sectional view of the pyrolysis apparatus in another example of the present invention.

In Example 1's pyrolysis apparatus for analysis, it is intended that sheet metal of good thermal conductivity is wound around the pyrolysis tube between the nichrome wire and the tube in the pyrolysis heater so that distribution of temperatures becomes even. According to FIG. 10 description will be made as follows:

Between a pyrolysis tube 1 and a nichrome wire 5 a sheet metal 19 is wound around pyrolysis tube 1, with a quartz glass tube 18 arranged outside. Quartz glass tube 18 is provided for the purpose of insulation. Then, sheet metal 19 keeps distribution of temperatures inside the pyrolysis tube even.

Figure 11:
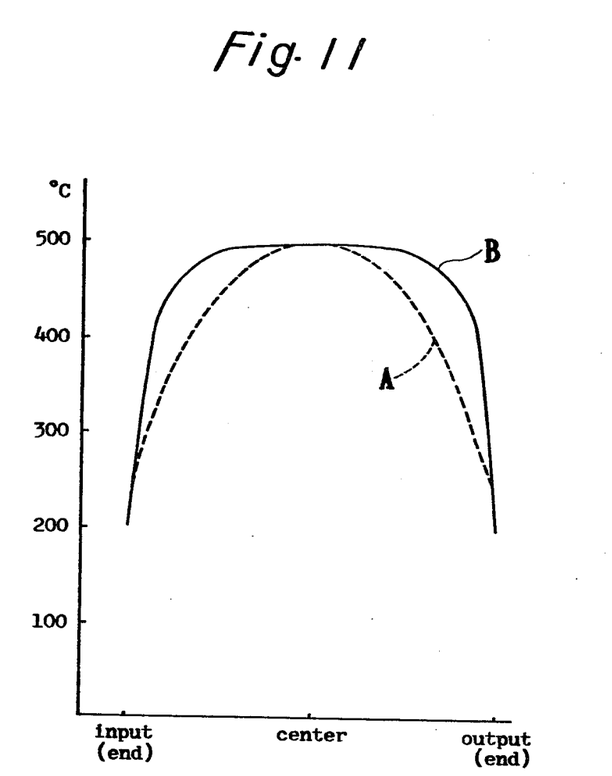
FIG. 11 is a distribution graph of temperatures at the heating portions in pyrolysis tube in FIGS. 2 and 10.

FIG. 11 is a graph showing a determined result of distribution of heating temperatures in pyrolyzed portions of Example 2's pyrolysis apparatus and the conventional one (FIG. 1). The set temperature in the pyrolysis central portion is 500° centigrade. Distribution of temperatures in the conventional pyrolysis apparatus demonstrates that as shown by dotted line A the temperatures drop sharply toward the end portions as they deviate from the central portion. On the other hand, distribution of temperatures in the example of the present invention demonstrates that as shown by dotted line B the temperatures hardly drop from the central portion to a certain area and the distribution is fairly even.

EXAMPLE 3

Figure 12:
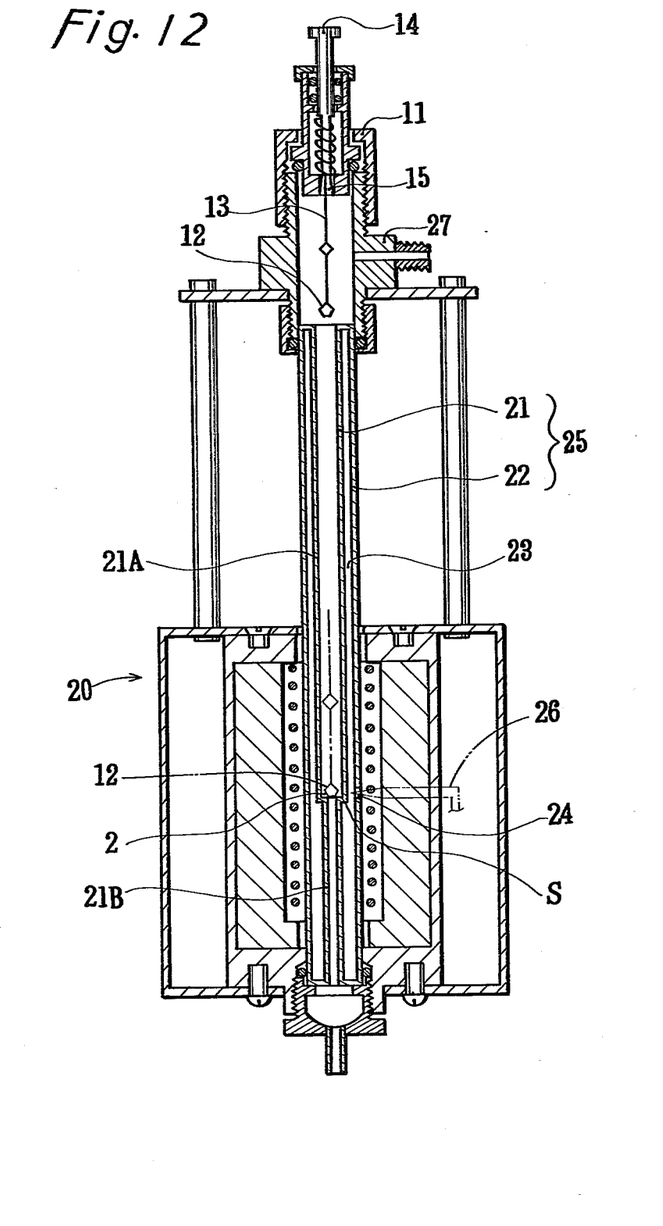
FIG. 12 is a vertical sectional view of the pyrolysis apparatus in still another example of the present invention.

In a pyrolysis apparatus for analysis in Example 1, wherein a pyrolysis tube is of a duplex structure, S stepped portion is formed right under the sample pyrolysis position of the inner tube and the lower portion of the tube being made of small tube. According to FIG. 12, the example will be described as follows:

A pyrolysis tube 25 is vertically and concentrically provided with the identical length of an inner tube 21 and an outer tube 22, and the duplex tube construction is integrally formed with quartz glass and the like tightly sealing the lower and upper ends of an annular space portion 23 formed between the inner tube 21 and the outer tube 22. Inner tube 21 is comprised of a large tube portion 21A for the upper portion and a small tube portion 21B for the lower portion so that a stepped portion S is formed right under sample pyrolysis position 2, beyond which sample basket 12 is unable to drop. Wherein, in order that pyrolyzed sample gas alone may pass through the heating portion, the smaller the small tube portion 21B, the better the pyrolysis condition. And, around the heating central portion of the outer tube 22, an air vent 24 is provided for preventing inner pressure due to heat from generating in an annular space portion 23.

The embodiment of Example 3 will now be described.

In the vertical type pyrolysis apparatus of Example 1, a pyrolysis tube 25 is built in and a thermocouple 26 is inserted from air vent 24. As aforementioned, to pyrolyze the sample, it is loaded in a sample basket 12 and by holding it with a detachable device 15 the basket is inserted from a sample inserting pipe 27 into the upper end portion of pyrolysis tube 25, and the holding mechanism of detachable device 15 is released, thereby the sample basket 12 drops due to the force of gravity, stops at stepped portion S and the sample is pyrolyzed at sample pyrolysis position 2.

Wherein, the resulting sample gas of the pyrolyzed sample at sample the pyrolysis position 2 is scarcely subject to secondary pyrolysis because the portion under sample pyrolysis position 2 is thinned so as to be a small tube 21B and the gas may be passed through the tube 21B with the carrier gas at a rapid velocity. And, due to duplex construction of the pyrolysis tube 25, the inside diameter of the tube becomes small compared with the conventional one, the eccentricity of dropping the position of the sample basket 12 is small and heat is evenly applied to the sample, so that pyrolysis of the sample becomes even. Moreover, gas inside inner tube 21 is slightly subject to atmospheric temperatures because outside annular space portion 23 of inner tube 21 works as an insulation space.

And, a thermocouple 26 may be easy of access to sample basket 12 at the central heating portion, so that the pyrolysis temperature can be accurately determined.

EXAMPLE 4

Figure 13:
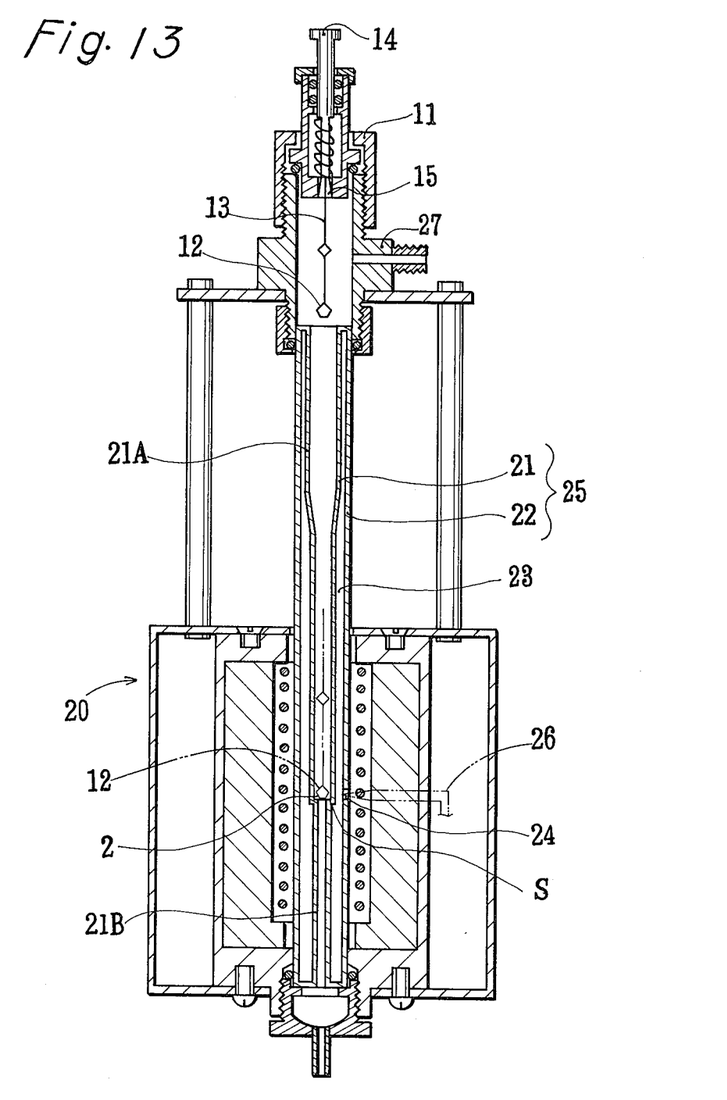
FIG. 13 is a vertical sectional view of the pyrolysis apparatus in yet another example of the present invention.

In the pyrolysis apparatus for analysis in Example 3, the upper large tube portion of the inner tube for the pyrolysis tube is formed tapered downwards. According to FIG. 13, the example will be described as follows:

The intermediate portion of large tube portion 21A of inner tube 21 is reduced or tapered downwards, so that upon free dropping of the sample basket 12 it is not hanged by the upper end portion of inner tube 21, but ready for dropping into the central portion of stepped portion S.

Since the present invention has such structure as in the preceding examples, it has such effects as follows:

1. free dropping of the sample due to force of gravity of the sample basket removes inconvenience in introducing the sample as in those of conventional horizontal types and facilitates good reproducibility.
2. Small amount (about 0.1mg) of the sample at the bottom of the sample basket drops freely with the basket and there is no risk of being spilled on the way.
3. Because no skill is required there is slight difference in data between individuals, laboratories or experiments.

Due to the free dropping, the sample basket drops steadily and vertically on a definite position and hardly contacts with the tube wall.

In addition to the above effects,

5. In Example 2, distribution of temperatures in the heating portion is even.
6. In Examples 3 and 4, the resulting pyrolysis products are not subject to secondary pyrolysis and pyrolysis of the sample becomes even.

That is, compared with the conventional invention, the present invention makes available data having good reproducibility with slight difference between laboratories, workers or experiments as well as very accurate analytical data.

The above-mentioned sample basket is made from platinum or silver and does not break when dropped down into position.

We claim:

1. A pyrolysis and analyzing apparatus comprising, a vertical tube, means for releasably suspending in said tube a sample of a material to be pyrolyzed and the decomposition gases thereof analyzed, means for introducing an inert carrier gas into said tube for transporting the decomposition gases to be analyzed, means defining a rest position within said tube through which said inert carrier gas can pass axially of said tube and to which said sample is dropped and held for heating until decomposed and gasified, means externally of said tube for heating said sample at said rest position, and means for said inert carrier gas transporting the gas to be analyzed can exit from said tube downstream of said rest position.

2. A pyrolysis and analyzing apparatus according to claim 1, in which said means for releasably suspending said sample comprises an open receptacle containing the sample, a suspension rod on which said receptacle is hung, and means for releasably clamping the rod and holding it depending therefrom.

3. A pyrolysis and analyzing apparatus according to claim 2, in which said tube comprises a reduced diameter portion axially spaced downwardly from the receptacle when suspended in use and defining a restriction internally of the tube for receiving the receptacle when dropped and holding the receptacle and sample thereon at said rest position for decomposition and gasification of said sample at said rest position.

4. A pyrolysis and analyzing apparatus according to claim 2, in which said means defining said rest position comprises a perforated plate across said tube internally thereof.

5. A pyrolysis and analyzing apparatus according to claim 2, in which said tube comprises a reduced diameter portion axially spaced downstream from the receptacle when suspended in use and defining a restriction internally of said tube for receiving the receptacle when dropped and holding the receptacle and sample thereon at said rest position, and a tapered portion downstream of the receptacle terminating in a portion of reduced diameter greater in diameter than the first-mentioned reduced diameter portion and terminating in said first-mentioned reduced diameter portion.

6. A pyrolysis and analyzing apparatus according to claim 1, in which said means for releasably suspending said sample comprises an open receptacle made of a material capable of being heated and unbreakable when dropped to said rest position, means for holding the receptacle depending comprising a clamp-like device depressable manually for releasing the receptacle on upon being depressed and having a resilient clamp opened when the device is depressed.

7. A pyrolysis and analyzing apparatus according to claim 1, including means to distribute heat evenly along an axial length of said tube including said rest position.

8. A pyrolysis and analyzing apparatus according to claim 7, in which said means to distribute heat evenly comprises a metallic band about said tube.

9. A pyrolysis and analyzing apparatus according to claim 1, including means for sensing the temperature within said tube at said rest position and developing a signal externally of the tube representative of and corresponding to said temperature.

* * * * *